United States Patent
Weng et al.

(10) Patent No.: US 11,931,536 B2
(45) Date of Patent: Mar. 19, 2024

(54) SURFACE LIQUEFIED DRUG-COATED BALLOON

(71) Applicant: DK Medical Technology Co., Ltd., Suzhou (CN)

(72) Inventors: Yulin Weng, Suzhou (CN); Quan Shi, Suzhou (CN); Baorui Liu, Suzhou (CN); Zhuoyang Gu, Suzhou (CN)

(73) Assignee: DK Medical Technology Co., Ltd., Sozhou (CN)

(*) Notice: Subject to any disclaimer, the term of this patent is extended or adjusted under 35 U.S.C. 154(b) by 746 days.

(21) Appl. No.: 16/634,031

(22) PCT Filed: Jul. 26, 2017

(86) PCT No.: PCT/CN2017/094445
§ 371 (c)(1),
(2) Date: Jan. 24, 2020

(87) PCT Pub. No.: WO2019/019043
PCT Pub. Date: Jan. 31, 2019

(65) Prior Publication Data
US 2020/0197673 A1    Jun. 25, 2020

(51) Int. Cl.
| | |
|---|---|
| A61M 31/00 | (2006.01) |
| A61F 2/82 | (2013.01) |
| A61K 31/20 | (2006.01) |
| A61K 31/337 | (2006.01) |
| A61K 47/14 | (2017.01) |
| A61L 29/16 | (2006.01) |

(Continued)

(52) U.S. Cl.
CPC ....... *A61M 25/1029* (2013.01); *A61K 31/337* (2013.01); *A61K 47/14* (2013.01); *A61M 25/104* (2013.01); *A61M 2025/1004* (2013.01); *A61M 2025/1031* (2013.01); *A61M 2025/105* (2013.01)

(58) Field of Classification Search
None
See application file for complete search history.

(56) References Cited

U.S. PATENT DOCUMENTS

| | | | | |
|---|---|---|---|---|
| 9,012,506 B2 * | 4/2015 | Faucher | ............... | A61P 41/00 |
| | | | | 514/183 |
| 9,737,640 B2 * | 8/2017 | Wang | ............... | A61L 29/08 |

(Continued)

FOREIGN PATENT DOCUMENTS

| | | |
|---|---|---|
| CN | 101918080 A | 12/2010 |
| CN | 102316922 A | 1/2012 |

(Continued)

OTHER PUBLICATIONS

International Search Report for International Application No. PCT/CN2017/094445 dated Apr. 20, 2018.

*Primary Examiner* — Ann Schillinger
(74) *Attorney, Agent, or Firm* — Foley Hoag LLP; Dana M. Gordon

(57) ABSTRACT

Disclosed are a drug-coated balloon and a method for preparing the same. The drug-coated balloon comprises a surface liquefied drug coating and a balloon, wherein the drug coating comprises a lipophilic excipient and a drug. The balloon can reduce the loss of the drug during delivery and increase efficiency in transferring the drug to a lesion site.

5 Claims, 2 Drawing Sheets

(51) Int. Cl.
*A61L 31/16* (2006.01)
*A61M 25/10* (2013.01)

(56) References Cited

U.S. PATENT DOCUMENTS

| | | | | |
|---|---|---|---|---|
| 2008/0118544 | A1* | 5/2008 | Wang | A61L 29/16 424/448 |
| 2009/0004281 | A1* | 1/2009 | Nghiem | A61K 31/554 424/490 |
| 2010/0233229 | A1* | 9/2010 | Nakagawa | A61L 31/16 424/85.4 |
| 2010/0331816 | A1* | 12/2010 | Dadino | A61K 31/08 604/509 |
| 2011/0144577 | A1* | 6/2011 | Stankus | A61P 9/10 514/291 |
| 2012/0028924 | A1* | 2/2012 | Aquila | C07F 9/65685 544/122 |
| 2012/0143132 | A1* | 6/2012 | Orlowski | A61L 29/16 604/103.02 |
| 2014/0178563 | A1 | 6/2014 | Bates et al. | |
| 2015/0224234 | A1* | 8/2015 | Wang | A61M 25/1029 514/291 |
| 2016/0213890 | A1* | 7/2016 | Kaufman | A61M 25/10 |
| 2020/0019673 | A1 | 1/2020 | Peng et al. | |

FOREIGN PATENT DOCUMENTS

| | | | | |
|---|---|---|---|---|
| CN | 202113470 | U | | 1/2012 |
| CN | 204840617 | U | | 12/2015 |
| CN | 106237395 | A | | 12/2016 |
| EP | 2729195 | B1 * | 8/2015 | ........... A61K 31/439 |
| ES | 2407660 | T3 * | 6/2013 | ............. A61L 31/14 |
| WO | WO-2007111885 | A2 * | 10/2007 | ............. A61L 27/34 |
| WO | WO-2011071630 | A1 * | 6/2011 | ........... A61L 29/085 |
| WO | WO-2013059509 | A1 * | 4/2013 | ....... A61B 17/12136 |
| WO | WO-2016015874 | A1 * | 2/2016 | ........... A61K 31/337 |
| WO | WO-2016118923 | A1 | | 7/2016 |
| WO | WO-2018050916 | A1 * | 3/2018 | ........... A61F 2/0077 |
| WO | WO-2018114992 | A1 * | 6/2018 | ........... A61K 31/337 |

* cited by examiner

SURFACE LIQUEFIED DRUG-COATED BALLOON

FIELD OF THE INVENTION

The present invention relates to a surface liquefied drug-coated balloon, a method for preparing the same, and a use thereof for treating stenosis in blood vessels including coronary arteries, peripheral blood vessels and the like.

BACKGROUND ART

Atherosclerosis is a chronic inflammatory response in the arterial wall, primarily due to accumulation of blood cells and formation of plaques on the arterial wall by low-density lipoprotein. Atherosclerosis is the most common and most dangerous disease, often leading to thrombosis, vascular stenosis, blood supply disorders, etc. and further affecting other functions of the body.

Angioplasty is a vascular intervention technique involving mechanical widening of obstructed blood vessels usually caused by atherosclerosis. The general practice is inserting a catheter with a tightly folded balloon into a patient's vascular system and sending it to the lesion site where a certain pressure is applied to inflate the balloon. The balloon can be inflated to a certain diameter and length. Specifically, percutaneous coronary intervention (PCI) of coronary angioplasty is useful for treating coronary artery stenosis. Percutaneous transluminal angioplasty (PTA) for peripheral blood vessels is useful for treating blood vessels other than the coronary arteries.

In PCI surgery, the most commonly used instrument is a balloon catheter which comprises a balloon and a catheter tube, wherein the balloon is connected to the catheter tube and located at the distal end of the tube. A user of the balloon catheter may insert a balloon at the site of intravascular stenosis and inflate it for treatment at the site.

A drug-coated balloon catheter is a balloon catheter coated with a layer of drug on the balloon surface, which is useful for the treatment of stenosis in blood vessels including coronary arteries, peripheral blood vessels and the like. With the drug-coated balloon catheter, the drug can be evenly applied to diseased blood vessels without leaving behind any implants such as stents in the human body, thereby providing an opportunity for secondary treatment. It generally takes less than one minute to inflate the drug-coated balloon for coronary arteries during use. So the drug must be effectively transferred from the balloon surface to the blood vessel wall within one minute. Moreover, during the intravascular delivery of the drug balloon, blood flushing may result in a loss of the drug content on the balloon surface, and further negatively affect the drug from being transferred from the balloon surface to the lesion site.

Chinese patent application CN201010121627.4 designs a balloon having a concave-convex non-planar structure on its outer surface, so that an increased amount of the drug can be adsorbed, and at the same time, the drug adsorbed onto the outer wall of the balloon would be kept from being washed off by blood in blood vessels as much as possible. However, it would cause damage to the balloon, and affect its rated burst pressure.

Chinese patent application CN201110176942.1 introduces a method for preparing a drug balloon by electrostatic self-assembly. With the self-assembly method, balloons made of different materials can be coated with drugs. Electrostatic self-assembly entails a great number of cycles, so the amount of the drug can be added layer by layer. However, the amount of the drug assembled on the outer layer and the binding force tend to decrease, as the surface charge gradually decreases after cycling for three times.

Chinese patent application CN201410289533.6 uses a plasma etching method to form a nano-scale microporous structure on the surface of the balloon, so as to improve the binding force between the balloon surface and the drug coating, increase the drug load and avoid loss of the drug during delivery. However, plasma etching negatively affects the performance of the balloon, i.e., it may reduce the burst pressure of the balloon.

Therefore, the present invention is hereby proposed to reduce the loss of the drug caused by flushing during delivery, and to increase efficiency in transferring the drug from the balloon surface to a lesion site.

SUMMARY OF THE INVENTION

The present inventors have surprisingly and unexpectedly found that a liquefied drug coating can be formed on the balloon surface by mixing a lipophilic excipient and a drug at a certain ratio, dissolving them with a solvent and applying the solution onto the balloon surface. Compared with the prior art, the present invention uses a lipophilic excipient, and the coating on the balloon surface is a liquefied coating rather than a conventional solid coating.

The present invention aims to form a liquefied drug coating with a certain viscosity on the surface of the balloon. On the one hand, it may reduce drug loss; on the other hand, it may improve efficiency in transferring the drug to a lesion site. In order to fulfill the above purpose, a lipophilic excipient, a drug, and a solvent are mixed and prepared into a drug solution to be applied onto the surface of a balloon by spray coating.

When the solvent in the drug solution is volatilized, a drug coating composed of the drug and the excipient is formed on the surface of the balloon.

The use of a lipophilic excipient can prevent the drug from being washed off during the intravascular delivery. Moreover, the resulting liquefied coating can enable the drug to be transferred from the surface of the balloon to the lesion site quickly and effectively during a short period of contact with the lesion site, and the process of balloon inflation would not result in shedding of the drug from the balloon.

Thus, in one aspect of the present invention, there is provided a drug-coated balloon, comprising a surface liquefied drug coating and a balloon.

The drug coating comprises a lipophilic excipient and a drug.

In another aspect of the present invention, the lipophilic excipient comprises triglyceride, triacetin, tricaprin and caprylic triglyceride, preferably triglyceride.

In another aspect of the present invention, the drug comprises paclitaxel, docetaxel, albumin-bound paclitaxel, rapamycin, everolimus, temsirolimus, zotarolimus, Biolimus and tacrolimus. Preferably, the drug is paclitaxel.

In another aspect of the present invention, in the drug coating on the surface of the balloon, the drug accounts for 9% to 91%, preferably 20% to 50%, more preferably 30% to 40% of the total weight of the drug coating. The excipient accounts for 9% to 91%, preferably 50% to 80%, more preferably 60% to 70% of the total weight of the drug coating.

Preferably, the drug coating on the surface of the balloon is composed of paclitaxel and triglyceride, each accounting for 33% and 67% of the total weight of the drug coating.

In another aspect of the present invention, the drug is present in an amount of from 1 to 100 μg/mm², preferably from 2 to 5 μg/mm² on the surface of the balloon.

In another aspect of the present invention, the drug coating is liquefied.

In yet another aspect of the present invention, there is provided a method for preparing the drug-coated balloon, comprising the following steps:
a) a lipophilic excipient, a drug and a solvent are mixed at a certain ratio, heated while stirring to form a drug solution;
b) a balloon is folded;
c) the balloon is coated by spraying with the drug solution formed in step a);
d) the solvent is volatilized to form a drug coating on the surface of the balloon.

In another aspect of the present invention, the amount of each component of the drug coating layer based on the total weight of the drug solution may be as follows: the drug accounts for 1% to 90%, preferably 1% to 10%, more preferably 2% to 8%, most preferably 2% to 6% of the total weight of the drug solution; the excipient accounts for 1% to 90%, preferably 1% to 20%, more preferably 4% to 10% of the total weight of the drug solution; the solvent accounts for 5% to 98%, preferably 79% to 98%, more preferably 82% to 94% of the total weight of the drug solution.

In another aspect of the present invention, the lipophilic excipient comprises triglyceride, triacetin, tricaprin and caprylic triglyceride, preferably triglyceride.

In another aspect of the present invention, the drug comprises paclitaxel, docetaxel, albumin-bound paclitaxel, rapamycin, everolimus, temsirolimus, zotarolimus, Biolimus and tacrolimus. Preferably, the drug is paclitaxel.

In another aspect of the present invention, the solvent comprises acetone, water, methanol, ethanol, isopropanol, acetonitrile, ethyl acetate, and methyl formate. Preferably, the solvent is acetone.

Preferably, the drug solution is a mixture of paclitaxel, triglyceride and acetone, wherein paclitaxel, triglyceride and acetone are each preferably in the range of from 2% to 6%, 4% to 10% and 82% to 94% based on the total weight of the drug solution. More preferably, paclitaxel, triglyceride and acetone are each 2%, 4% and 94% based on the total weight of the drug solution.

In another aspect of the present invention, the lipophilic excipient, the drug, and the solvent are mixed at a certain ratio and coated by spraying onto the surface of the folded balloon. After the acetone is volatilized, the mixture of the excipient and the drug covers the surface of the balloon to form a liquefied drug coating.

The balloon folding process is generally as follows: the balloon is inflated to a certain pressure, and then folded using a balloon folding device. The balloon is cylindrical before folding, but it forms a certain number of wings after folding, with the resulting wings curled to protect the drug on the surface of the balloon and to reduce the outer diameter of the balloon.

In another aspect of the present invention, the balloon with a liquefied coating can be further shaped to protect the liquefied coating on the balloon.

The shaping process is generally as follows: the gas inside the balloon is withdrawn to form a negative pressure inside, and then the balloon would be shaped according to the folded shape.

Therefore, in another aspect of the present invention, there is provided a use of a drug-coated balloon obtained according to the present invention for the treatment of intravascular stenosis. The intravascular stenosis may be intracoronary stenosis or peripheral intravascular stenosis.

The present invention will now be described in particular by the following Examples.

DETAILED DESCRIPTION OF THE INVENTION

Figure 1:
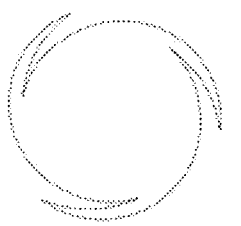
FIG. 1 is a cross-sectional view of a folded balloon according to a preferred embodiment of the present invention.
Figure 1:
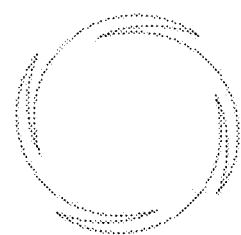
Figure 2:
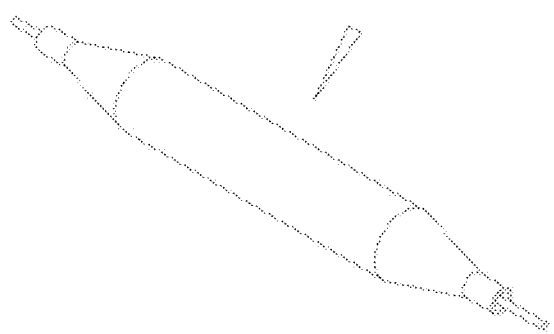
FIG. 2 is a schematic diagram of a balloon coating according to a preferred embodiment of the present invention.

Other aspects of the present invention will be described in detail below. Upon reviewing the following detailed description of the embodiments and the appended claims, these and other features of the present invention and the advantages thereof would be obvious.

Unless otherwise defined, all technical and scientific terms used herein have the same meaning as commonly understood by a person skilled in the field the present invention belongs to.

Example 1: Preparation of a Drug-Coated Balloon

Paclitaxel, triglyceride and acetone were mixed at a weight ratio of 2%, 4% and 94%, heated to 30° C., and stirred at a constant temperature for 30 minutes to form a drug solution.

The balloon was inflated to 1 atm, folded into 3 wings using a balloon folding device, and remained folded for 3 minutes while the temperature was increased to 45° C.

The drug solution was injected into a coating machine, with the ultrasonic power adjusted to 20 watts, the internal pressure of the balloon to 2 atm, and the rotation speed of the balloon to 3 revolutions per second, axial reciprocating motions were carried out at 2 mm/second. The whole course for completing the axial length of the balloon was counted as one cycle. A total of 10 cycles were required for spray coating. When acetone was volatilized, a drug-coated balloon was obtained.

Example 2: Preparation of a Drug-Coated Balloon

Paclitaxel, triglyceride and acetone were mixed at a weight ratio of 64%, 6% and 30%, heated to 30° C., and stirred at a constant temperature for 30 minutes to form a drug solution.

The balloon was inflated to 1 atm, folded into 3 wings using a balloon folding device, and remained folded for 3 minutes while the temperature was increased to 45° C.

The drug solution was injected into a coating machine, with the ultrasonic power adjusted to 20 watts, the internal pressure of the balloon to 2 atm, and the rotation speed of the balloon to 3 revolutions per second, axial reciprocating motions were carried out at 2 mm/second. The whole course for completing the axial length of the balloon was counted as one cycle. A total of 10 cycles were required for spray coating. When acetone was volatilized, a drug-coated balloon was obtained.

Example 3: Preparation of a Drug-Coated Balloon

Paclitaxel, triglyceride and acetone were mixed at a weight ratio of 15%, 50% and 35%, heated to 30° C., and stirred at a constant temperature for 30 minutes to form a drug solution.

The balloon was inflated to 1 atm, folded into 3 wings using a balloon folding device, and remained folded for 3 minutes while the temperature was increased to 45° C.

The drug solution was injected into a coating machine, with the ultrasonic power adjusted to 20 watts, the internal pressure of the balloon to 2 atm, and the rotation speed of the balloon to 3 revolutions per second, axial reciprocating motions were carried out at 2 mm/second. The whole course for completing the axial length of the balloon was counted as one cycle. A total of 10 cycles were required for spray coating. When acetone was volatilized, a drug-coated balloon was obtained.

Example 4: Preparation of a Drug-Coated Balloon

Paclitaxel, triglyceride and acetone were mixed at a weight ratio of 2%, 10% and 88%, heated to 30° C., and stirred at a constant temperature for 30 minutes to form a drug solution.

The balloon was inflated to 1 atm, folded into 3 wings using a balloon folding device, and remained folded for 3 minutes while the temperature was increased to 45° C.

The drug solution was injected into a coating machine, with the ultrasonic power adjusted to 20 watts, the internal pressure of the balloon to 2 atm, and the rotation speed of the balloon to 3 revolutions per second, axial reciprocating motions were carried out at 2 mm/second. The whole course for completing the axial length of the balloon was counted as one cycle. A total of 10 cycles were required for spray coating. When acetone was volatilized, a drug-coated balloon was obtained.

Example 5: Preparation of a Drug-Coated Balloon

Paclitaxel, triglyceride and acetone were mixed at a weight ratio of 4%, 16% and 80%, heated to 30° C., and stirred at a constant temperature for 30 minutes to form a drug solution.

The balloon was inflated to 1 atm, folded into 3 wings using a balloon folding device, and remained folded for 3 minutes while the temperature was increased to 45° C.

The drug solution was injected into a coating machine, with the ultrasonic power adjusted to 20 watts, the internal pressure of the balloon to 2 atm, and the rotation speed of the balloon to 3 revolutions per second, axial reciprocating motions were carried out at 2 mm/second. The whole course for completing the axial length of the balloon was counted as one cycle. A total of 10 cycles were required for spray coating. When acetone was volatilized, a drug-coated balloon was obtained.

Example 6: Preparation of a Drug-Coated Balloon

Paclitaxel, triglyceride and acetone were mixed at a weight ratio of 2%, 20% and 78%, heated to 30° C., and stirred at a constant temperature for 30 minutes to form a drug solution.

The balloon was inflated to 1 atm, folded into 3 wings using a balloon folding device, and remained folded for 3 minutes while the temperature was increased to 45° C.

The drug solution was injected into a coating machine, with the ultrasonic power adjusted to 20 watts, the internal pressure of the balloon to 2 atm, and the rotation speed of the balloon to 3 revolutions per second, axial reciprocating motion s were carried out at 2 mm/second. The whole course for completing the axial length of the balloon was counted as one cycle. A total of 10 cycles were required for spray coating. When acetone was volatilized, a drug-coated balloon was obtained.

Example 7: Preparation of a Drug-Coated Balloon

Paclitaxel, triglyceride and acetone were mixed at a weight ratio of 6%, 24% and 70%, heated to 30° C., and stirred at a constant temperature for 30 minutes to form a drug solution.

The balloon was inflated to 1 atm, folded into 3 wings using a balloon folding device, and remained folded for 3 minutes while the temperature was increased to 45° C.

The drug solution was injected into a coating machine, with the ultrasonic power adjusted to 20 watts, the internal pressure of the balloon to 2 atm, and the rotation speed of the balloon to 3 revolutions per second, axial reciprocating motions were carried out at 2 mm/second. The whole course for completing the axial length of the balloon was counted as one cycle. A total of 10 cycles were required for spray coating. When acetone was volatilized, a drug-coated balloon was obtained.

Example 8

The drug-coated balloons according to Examples 1-7 of the present invention was subjected to viscosity measurement, and an electron microscope (Leica DM4000M metallographic microscope) was used to observe surface uniformity of a commercially available Braun drug balloon and the drug-coated balloon according to Examples 1-7.

Viscosity:

The drug coating of the present invention was liquefied, adhering to the surface of the balloon. As for the drug coating, an advantageous viscosity ranged from about 500 cp to 5000 cp, more preferably from 500 cp to 1000 cp, and most preferably from 800 cp to 1000 cp. It was found that the viscosity of the drug coating according to Examples 1-7 of the present invention ranged from about 500 cp to 5000 cp, while the drug coating of the Braun drug balloon was a solid coating and therefore could not be characterized by viscosity.

TABLE

Viscosity of the Examples of the present invention

| | Examples | | | | | | |
|---|---|---|---|---|---|---|---|
| | 1 | 2 | 3 | 4 | 5 | 6 | 7 |
| Viscosity | 800 | 3000 | 1000 | 1200 | 1000 | 500 | 1000 |

A liquefied drug coating with a suitable viscosity can facilitate the attachment of the drug coating to the balloon, and prevent the balloon from being washed off by the blood when passing through the blood vessel.

Figure 3:
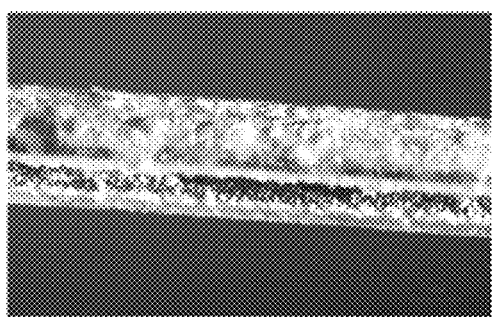
FIG. 3 is an electron microscope image of a commercially available Braun drug balloon and a drug balloon according to Example 1 of the present invention. The picture on the left shows a commercially available Braun drug balloon, while the picture on the right shows a drug balloon according to Example 1 of the present invention.
Figure 3:
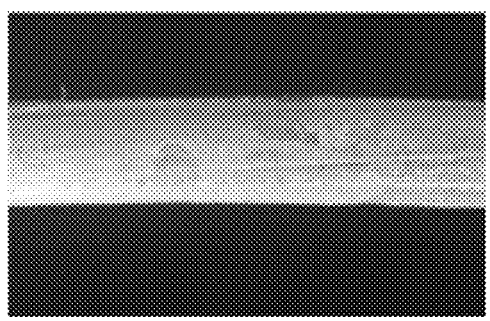
Figure 4:
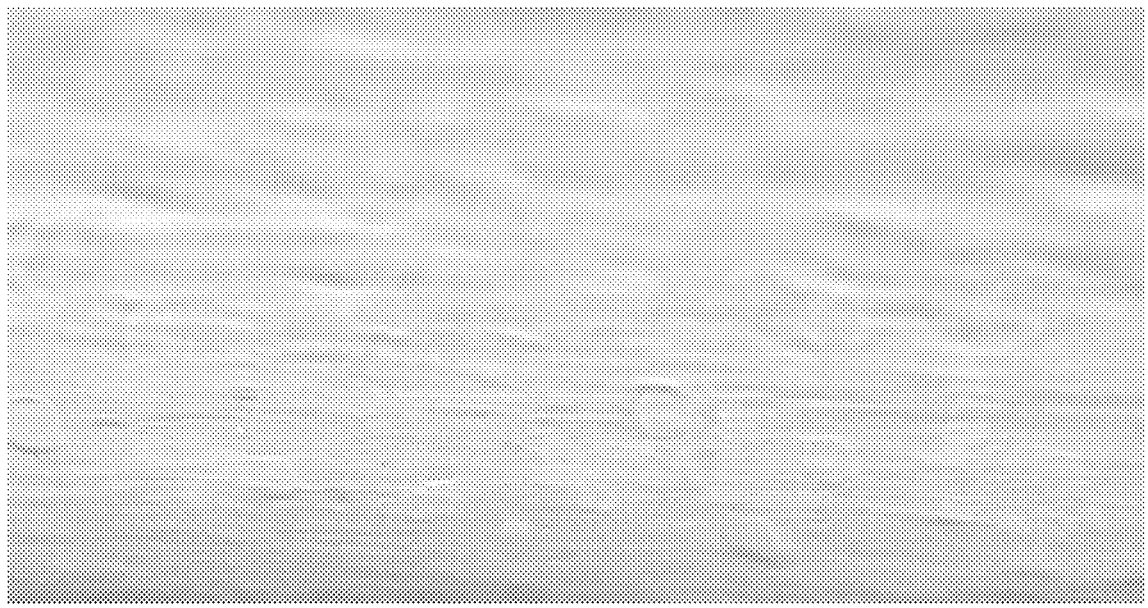
FIG. 4 is an electron microscope photograph of a drug balloon according to Example 1 of the present invention.

Electron Microscopy:

It can be seen from FIG. 3 that in the left picture, the drug on the surface of the Braun drug balloon has a granular shape, and is unevenly distributed on the surface of the balloon. When the drug on the balloon surface is unevenly distributed, this increases roughness of the balloon surface, and further increases the shearing force between the drug on the balloon surface and the blood. As a result, the drug on the balloon surface would be more easily washed off by the blood during delivery of the balloon catheter. In addition, when drug particles of uneven sizes on the surface are in contact with the lesion site, only a part of the particles can be attached to the blood vessel wall, which is unconducive to releasing the drug to the blood vessel wall.

By contrast, the balloon drug according to Example (1) of the present invention (FIG. 3, the right picture) covers the entire surface of the balloon, and is evenly distributed, which reduces the shearing force between the balloon and the blood, facilitates delivery, and can reduce flushing off the drug by the blood. Meanwhile, as the drug is in a liquefied state, it would be more easily adhered and further released to the blood vessel wall.

Example 9: Experiment on Drug Shedding Rate

The experiment on drug shedding rate is used to characterize the percentage of the drug flushed off by the blood during delivery of drug balloon, based on the weight of the drug loaded on the balloon. This experiment employs a simulation test, comprising the following experimental steps:
a) inserting a guide wire into a guide wire cavity of a balloon catheter;
b) advancing the drug-coated balloon catheter along the guide wire to simulate a surgical application;
c) advancing the balloon to a target simulated lesion site;
d) directly withdrawing the balloon without inflating the balloon;
e) eluting the remaining drug on the withdrawn drug balloon;
f) determining the amount of the drug residue M1 on the withdrawn balloon using a high-performance liquid.

Shedding rate=$(Mn-M1)/Mn \cdot 100\%$, wherein Mn is the nominal content of the drug.

The measured results are as follows:

TABLE 2

Drug shedding rates of the Examples of the present invention and the Braun drug balloon

| | Examples | | | | | Commercially available Braun drug balloon |
|---|---|---|---|---|---|---|
| | 1 | 2 | 3 | 4 | 5 | |
| Drug shedding rates | 12% | 15% | 17% | 13% | 14% | 33% |

The shedding rate of the drug during delivery indicates the firmness of the drug coating on the balloon. The lower the shedding rate is, the less the drug is lost during delivery, and the more the drug reaches the target location to achieve the therapeutic effect. It can be known from Table 2 that the drug shedding rate of Examples 1-5 of the present invention is far lower than the drug shedding rate of the commercially available Braun drug balloon. This shows that compared with the commercially available Braun drug balloon, the drug-coated balloon of Examples 1-5 of the present invention has attached drug more firmly to the balloon, fewer drug lost during delivery, and more drug reaching the target location.

Example 10: Content/Time Curve of the Drug in Blood Vessels

The content/time curve of the drug in blood vessels is used to characterize the change of the drug remaining on blood vessels over time, after the drug balloon is attached to blood vessels. When dilating a narrow blood vessel, the drug balloon would cause tearing of the vascular intima. This requires use of the drug to inhibit hyperplasia and further reduce restenosis. Restenosis is a chronic process requiring repeated administration of the drug over a long period of time. Thus, it is essential to ensure continuous drug release through topical drug delivery to prevent restenosis. Therefore, the decay of the drug content in blood vessels over time is vital to preventing restenosis.

The content/time curve of the drug in blood vessels was derived by experimenting on animals. Miniature pigs are recognized as standard animals in experimental studies. Among them, panama minipigs, in view of their small size and similarity to humans in various organs and physiological and biochemical indicators, are excellent experimental animals, and they are animal models for studying coronary heart disease. Therefore, this test used minipigs as experimental animals. The experimental steps were as follows:
a) after pigs were anesthetized, skin preparation, disinfection, and draping were performed at the groin; ECG, blood pressure, blood oxygen saturation, and temperature were continuously monitored; and blood pressure and left ventricular ejection fraction were measured once;
b) a 6/7 F sheath was implanted by a femorotomy;
c) a 6 F L (or R) 3.5 contrast catheter was used for contrast imaging, a surgery on blood vessels which had a balloon-to-blood vessel ratio of about 1.2 to 1.4 was performed, and the blood vessel diameter was observed and recorded, in line with the standard operating specification, the imaging was recorded with a imaging machine;
d) after coronary angiography, a test sample or a control sample was sent to the target vessel location along a PTCA guide wire, dilated at a pressure of 10 atm for 30 s, and the balloon catheter was then withdrawn; the imaging of the dilated balloon was recorded and stored with the imaging machine;
e) the coronary angiography was immediately checked to determine whether the blood flow was unobstructed, whether the blood vessels had dissection and thrombosis, and each indicator was evaluated;
f) the catheter was withdrawn, the surgical incision at the right groin was treated, and the pig was checked for health condition;
g) after the surgery using the drug-coated balloon of Example 1 of the present invention was performed, 2 animals was sacrificed each time at 30±3 min, 1 d±2 h, 7 d±4 h, 14 d±4 h, 28 d±1 d, and 90 d±3 d, respectively; after the surgery using the Braun drug balloon as a control sample was performed, 1 animal was sacrificed each time at 30±3 min, 1 d±2 h, and 7 d±4 h, respectively; after the animals were sacrificed, the blood vessels where the balloon was dilated were dissected and separated from the myocardium;

h) the blood vessels were weighted and homogenized to obtain tissue homogenate which was centrifuged to obtain a supernatant for sampling and detection by LC-MS/MS;

i) the drug concentration in the blood vessels at each time point was calculated, and concentration-time curves were drawn.

Figure 5:
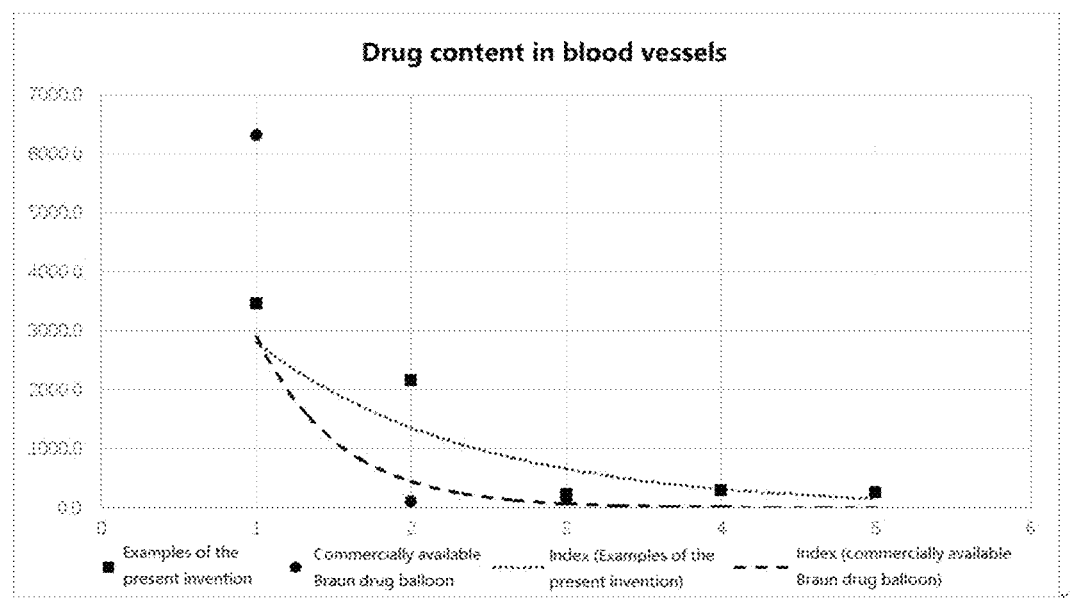
FIG. 5 is a schematic diagram of the drug content of a drug balloon according to Example (1) of the present invention and a commercially available Braun drug balloon at different time.

The results are shown in FIG. 5 which is a schematic diagram of the drug content of a drug balloon according to Example (1) of the present invention and a commercially available Braun drug balloon at different time.

It can be seen from FIG. 5 that the decay rate of the drug content in blood vessels over time in the Example of the present invention is lower than that of the Braun drug balloon product. This shows that the drug of the Example of the present invention remains in blood vessels for a longer time, which is beneficial to continuously inhibiting intimal hyperplasia and reducing the occurrence of restenosis.

The present invention is not limited to the above embodiments, and a person skilled in the art would understand that various modifications, additions and substitutions can be made without departing from the scope and spirit of the present invention disclosed in the appended claims.

The invention claimed is:

1. A drug-coated balloon comprising a surface liquefied drug coating and a balloon, wherein the drug coating consists of a lipophilic excipient and a drug, the drug accounts for 20% to 50% of the total weight of the drug coating, the lipophilic excipient accounts for 50% to 80% of the total weight of the drug coating, and the lipophilic excipient is a triglyceride.

2. The drug-coated balloon of claim 1, wherein the drug comprises paclitaxel, docetaxel, albumin-bound paclitaxel, rapamycin, everolimus, temsirolimus, zotarolimus, Biolimus and tacrolimus.

3. The drug-coated balloon of claim 1 or 2, wherein the drug accounts for 30% to 40% of the total weight of the drug coating, and the excipient accounts for 60% to 70% of the total weight of the drug coating.

4. A method of treating intravascular stenosis in a patient in need thereof, comprising inserting the drug-coated balloon of claim 1 or 2 at the site of intravascular stenosis in the patient.

5. The method of claim 4, wherein the intravascular stenosis is intracoronary stenosis or peripheral intravascular stenosis.

* * * * *